United States Patent [19]

Weaver et al.

[11] 4,408,614

[45] Oct. 11, 1983

[54] BLOOD PRESSURE MEASUREMENT WITH KOROTKOV SOUND ARTIFACT INFORMATION DETECTION AND REJECTION

[75] Inventors: Charles S. Weaver, Palo Alto; Constance T. Chittenden, Los Altos, both of Calif.

[73] Assignee: SRI International, Menlo Park, Calif.

[21] Appl. No.: 280,798

[22] Filed: Jul. 6, 1981

[51] Int. Cl.³ .............................................. A61B 5/02
[52] U.S. Cl. ................................... 128/680; 128/682; 128/683
[58] Field of Search ....................... 128/680, 682–683

[56] References Cited

U.S. PATENT DOCUMENTS 4,116,230  9/1978  Gorelick .............................. 128/682
4,216,779  8/1980  Squires et al. ....................... 128/682

OTHER PUBLICATIONS

Weaver, C. S. et al., "A Study of Non-Invasive BP Measurements", *Non-Invasive Cardiovascular Measurements*, Society of Photo-Optical Instrumentation Engineers, 1978, vol. 167, pp. 89–105.

Primary Examiner—Kyle L. Howell
Assistant Examiner—Francis J. Jaworski
Attorney, Agent, or Firm—Victor R. Beckman

[57] ABSTRACT

Method and apparatus for recurrently obtaining systolic and diastolic blood pressure measurements, and measurements of the systolic slope of the blood pressure wave in a subject's artery are disclosed. Artifact information in Korotkov sound signals employed in the apparatus are substantially eliminated to avoid errors which otherwise normally are present in such measurements.

14 Claims, 9 Drawing Figures

BLOOD PRESSURE MEASUREMENT WITH KOROTKOV SOUND ARTIFACT INFORMATION DETECTION AND REJECTION

ORIGIN OF THE INVENTION

The Government has rights to this invention pursuant to NIH Grant No. HL-17604-01A1.

BACKGROUND OF THE INVENTION

Numerous means for obtaining blood pressure measurements are known including both invasive and noninvasive means. A number of noninvasive measuring means are disclosed in an article by C. S. Weaver, J. S. Eckerly, P. M. Newgard, C. T. Warnke, J. B. Angell, S. C. Terry, and J. Robinson, entitled "A Study of Non-Invasive Blood Pressure Measurement Techniques" presented at a conference held at Stanford University on September, 1978 and published by the Society of Photo-Optical Instrumentation Engineers. Included in the article is a description of an algorithm for processing cuff pressure measurements and associated R-wave peak detector and Korotkov sound detector output signals for detecting artifact information in the output from the Korotkov sound detector and eliminating said artifacts from the blood pressure measurements. The present invention involves an improved Korotkov sound processing algorithm.

SUMMARY OF THE INVENTION AND OBJECTS

An object of this invention is the provision of an improved method of identifying false signals in the output from a Korotkov sound detector employed in apparatus for the measurement of blood pressure and/or systolic slope of blood pressure waves in an artery of a subject.

An object of this invention is the provision of an automatic computer-implemented technique for identifying and eliminating false outputs from a Korotkov sound detector included in a blood pressure measuring system, or the like, which technique is well adapted for use during stress testing, or in an operating room and intensive care units of hospitals where ECG signals normally are available.

The above and other objects and advantages of this invention are achieved by means of a system which includes an inflatable cuff which is inflatable to a pressure above systolic pressure and deflatable to a pressure below diastolic pressure. A pressure transducer connected to the inflatable cuff generates a signal which is a function of cuff pressure. A microphone picks up Korotkov sounds, and artifacts, during deflation of the cuff, and electrodes attached to the subject pick up electrocardiographic signals. The peak of the ECG R-wave is detected by R-wave peak detection techniques. Many, but not all artifacts, are removed from the microphone output by use of K-sound detection techniques. The pressure transducer output is converted to digital form for transfer to a digital computer and storage in the computer memory. The time of arrival of the peak R-wave signals and associated K-sound and artifact signals also is stored in the computer memory. RK intervals comprising the time interval between the time of arrival of an R-wave signal and the associated K-sound or artifact signal are determined which, together with the associated cuff pressure, establish a plurality of RK interval versus cuff pressure points, some of which are true points and others of which are artifact points. These points are stored in the computer memory. Certain RK interval values outside normal ranges are eliminated as probably resulting from artifacts. Remaining RK intervals are grouped in separate groups using a chaining operation which involves estimating from one point at a high cuff pressure, an RK interval value, $\hat{RK}$, at a next lower cuff pressure at which there is a point. If the difference between the RK interval value at said lower cuff pressure and estimated interval value, $\hat{RK}$, is within a selected range, the actual value is added to the group. Now, using the newly added point, an estimated RK interval value for the next lower cuff pressure at which there is another point, is calculated and the difference between the estimated value $\hat{RK}$ and actual RK interval value is determined. Again, the point is added to the group of points if the difference is within a predetermined range of RK interval values. If the difference is outside the range, the point is not added to the group of points, and the RK interval at the next lower cuff pressure containing a point is checked. After the point at the lowest cuff pressure has been checked, the process is repeated starting at the highest ungrouped point. When all of the points have been grouped, the group with the greatest number of RK interval vs cuff pressure points therein is selected as the group which includes the greatest number of valid, or true, RK interval versus cuff pressure points. A straight line using minimum mean-square fitting techniques is fitted to these points and, with further processing, some additional artifact points may be deleted from the group. With artifact points deleted, the cuff pressure at the maximum and minimum RK interval points provides a measure of the subject's systolic and diastolic blood pressures, respectively. Using the techniques of this invention, accurate blood pressure measurements may be obtained with ambulatory subjects in a noisy environment.

BRIEF DESCRIPTION OF THE DRAWINGS

The invention will be better understood from the following description when considered with the accompanying drawings. In the drawings:

As is understood, electrocardiographic signals picked up by electrodes attached to a subject's body include a large R-wave component which is relatively easily detected. In FIG. 1, successive outputs from a peak R-wave detector included in the present system are identified by reference characters R1, R2–R20. At any given level of physical activity substantially periodic peak R-wave signals are produced by the subject, and, for simplicity, periodically occuring R-wave signals are shown in FIG. 1. An inflatable cuff attached to the upper arm of the subject is inflated and slowly deflated as shown by the plot of cuff pressure versus time included in FIG. 1. The cuff is inflated to a pressure, P, above systolic pressure, then is deflated through a pressure range at which Korotkov sounds are produced. A microphone at the inflatable cuff senses Korotkov sounds during deflation of the cuff. The microphone output is coupled to a Korotkov sound detector, the output from which includes true K-sounds identified by reference characters K8 through K20. In FIG. 1 the numerical suffixes 1 through 20 for the R-wave detector output identify the successive heartbeat periods, with corresponding suffixes being used for the K-sound detector and pressure transducer outputs K and P, respectively.

In FIG. 1, the Korotkov sound detector output is depicted on two lines, the upper one of which includes only artifact-free K-sounds, and the lower one of which includes only artifacts. The letter suffix A identifies those K sound detector outputs which are artifacts, and where more than one artifact output is produced during a given heartbeat period, a subsequent numerical suffix is included to separately identify the same. Thus, in FIG. 1, for heartbeat period 14, two K-sound artifact signals K14A1 and K14A2 are shown. For heart beat periods 3, 7 and 9, only one artifact per beat is shown, which are identified by reference characters K3A, K7A and K9A, respectively. In signal processing for the removal of artifacts from true K-sounds, use is made of the time interval between the occurrence of the R-wave and the subsequent occurrence of the associated K-sound detector output. Such RK intervals are identified by reference characters RK together with a numerical suffix for the associated heart beat periods. Where the K-sound detector output comprises an artifact, an additional suffix A is included, and if more than one artifact per heart beat period is produced, a subsequent numerical suffice distinguishes between the same. Thus, in FIG. 1, RK intervals for true Korotkov sounds are identified by reference characters RK8 through RK20 while RK intervals for artifacts are identified by the reference characters RK3A, RK7A, RK9A, RK14A1 and RK14A2.

Reference now is made to FIG. 2 of the drawings wherein a plot of RK interval measurements as a function of cuff pressure is shown. In FIG. 2, the plot includes RK interval measurements obtained using true K-sounds only, and not artifacts. Such RK interval versus cuff pressure points are identified as "true" points herein to distinguish the same from "artifact" points obtained using K-sound detector outputs which are artifacts. For the artifact-free plot shown in FIG. 2, a straight line 20 with a positive slope can be fitted through the series of points using minimum mean-squared fitting techniques. The slop, $\Delta$RK interval/$\Delta$ pressure, of the line 20, is inversely proportional to the systolic slope of the blood pressure wave of the subject and, therefor, provides a measure of the systolic slope of the blood pressure wave. The systolic slope of the blood pressure wave, and hence the slope of line 20, varies in accordance with exercise, with the systolic slope generally slowly increasing with increasing exercise. At rest, before exercise, a slope of approximately 1 (one) for line 20 is typical. In the operation of this invention a "control slope" $m_c$ is computed using an estimated slope of, say, 1 for the line 20 with the subject is at rest, before exercise. Measurements of slope are described in detail below. Also, the maximum and minimum cuff pressures at which true Korotkov sounds are obtained provide a measure of the systolic and diastolic blood pressures, respectively, as seen in FIG. 2.

For an ambulatory subject, or one undergoing stress exercise, the K-sound detector output includes numerous artifacts. In FIG. 3, to which reference now is made, a plot of RK interval measurements as a function of cuff pressure is shown which includes not only true points but also includes artifact points. A straight line 22 is shown fitted to the points using minimum means-squared fitting techniques. Although the slope of the line 22 may approximate that of a curve fitting to only true points, artifact points must be substantially eliminated from the plot if a relatively true measure of systolic slope and/or of systolic or diastolic blood pressure is to be obtained from the detected R-waves and K-sounds and associated cuff pressure measurements. An algorithm using cuff pressure measurements and times of occurrence of R-wave and K-sound outputs for identifying artifacts in order that they may be deleted from the K-sound output is described below. First, however, a simplified showing of a system which may be used for implementing such an algorithm will be described, which system includes means for obtaining necessary measurements of cuff pressure along with measurements of the time of arrival of R-waves and K-sounds.

Figure 4:
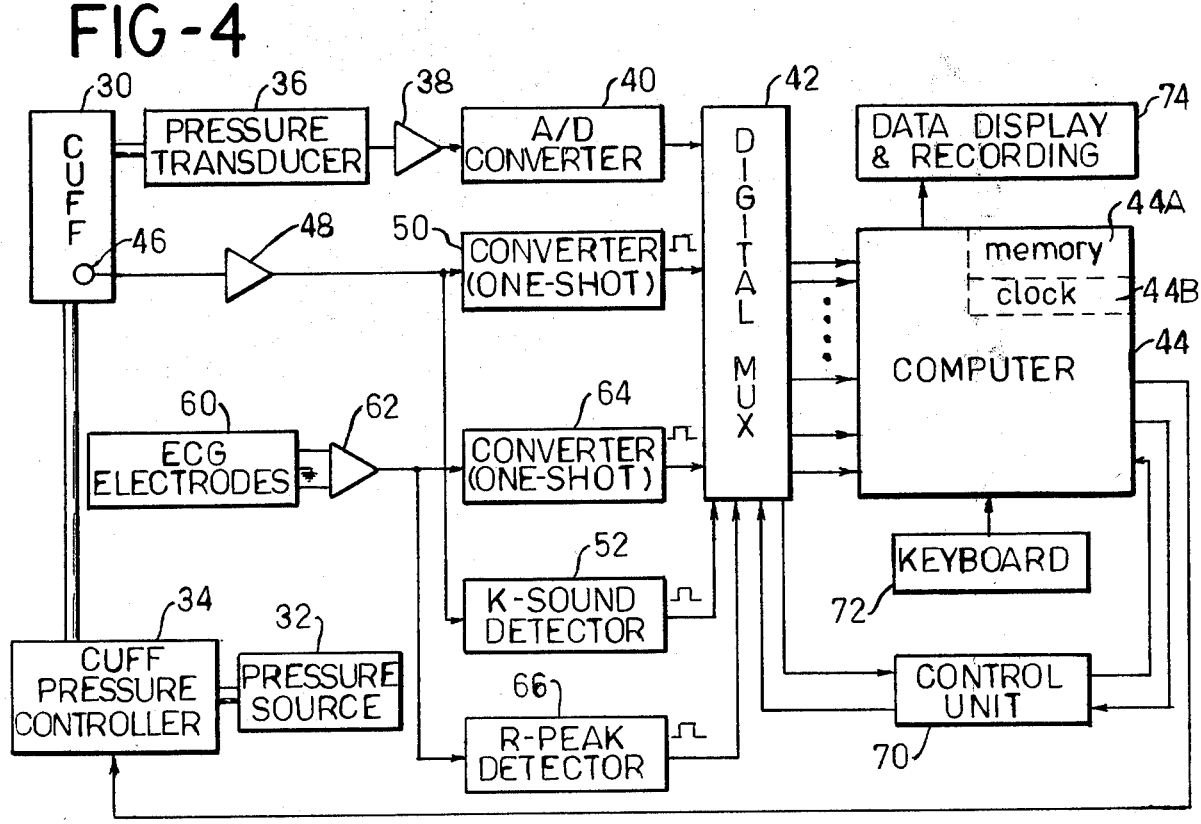
FIG. 4 is a simplified block diagram of a system which may be employed in the practice of this invention for identifying and deleting K-sound artifacts fro the output of K-sound detector means.

Reference now is made to FIG. 4 wherein a system which is suitable for use in the practice of this invention is shown comprising an inflatable cuff 30 for encircling a subject's limb, such as upper arm, and a pressure source 32 connected to the cuff through a pressure controller 34. Cuff pressure is sensed by a pressure transducer 36, the analog output from which is connected through an amplifier 38 to the input of an analog to digital converter 40 for conversion to digital signal form. The digitized cuff pressure signal is connected through a digital multiplexer 42 to a computer 44 which includes memory 44A where cuff pressure signals obtained during a cuff deflation temporarily are stored for use in computer systolic and diastolic blood pressure and/or the systolic slope of the blood pressure waves during said cuff deflation.

With the cuff attached to the upper arm of the subject, the cuff is inflated to a pressure above systolic pressure. Then, as the cuff pressure is decreased, by R-wave-triggered decrementation, the first Korotkov sound appears at the systolic pressure, and the last at the diastolic pressure. A microphone 46 picks up the Korotkov sound (K-sound) at a plurality of cuff pressures between systolic and diastolic pressures. The microphone also picks up noise; the amount of noise produced depending upon the physical activity of the subject. The microphone output signal is amplified by amplifier 48, and the amplifier output is supplied both to a signal converter 50 and a K-sound detector 52. The converter 50 simply may include a one-shot for generation of a pulse output in response to an amplified output signal from amplifier 48, which pulse output is connected to the multiplexer 42. The K-sound detector 52 distinguishes between true K-sounds and some artifacts, and produces an output in response to true K-sounds and artifacts which are not eliminated by the detector. The K-sound detector output is connected to an address input of the multiplexer 42. In the presence of an output from the K-sound detector, the output from converter 50 is connected through the multiplexer 42 to an interrupt input of the computer 44 to produce a K-sound, or artifact, timing signal which, together with an associated R-wave timing signal, provides a measure of the RK interval.

ECG electrodes 60 attached to the subject's body pick up ECG signals which are amplified by amplifier 62 and then supplied to a converter 64 and to an R-peak detector 66. As with the converter 50, the converter 64 also may include a one-shot for generation of a pulse output in response to the R-wave component of the amplified ECG signal. The pulse output from the converter 64 is connected to the multiplexer 42 for connection as an interrupt input to the computer 44. The R-peak detector detects the R-wave of the ECG signal while discriminating against noise and other ECG signal components, such as the P and T wave components. The R-peak detector output is supplied as an address input to the multiplexer 42 for connection of the output from the converter 64 to an interrupt input of the computer 44 when an R wave is detected. The difference in time between the arrival of an R wave input and associated true and/or artifact K-sound signal(s) at the interrupt inputs to the computer provides a measure of the RK and/or RKA interval, which interval value is temporarily stored in the computer memory 44A for use with other such true and artifact K-sound interval values obtained at different cuff pressures. A clock 44B is included in the system for use in making the above-described time interval measurements.

Another address input for the multiplexer 42 is obtained from the computer 44 through a control unit 70. Under control of unit 70, the multiplexer 42 is switched for connection of cuff pressure signals from the A/D converter 40 to the computer 44. Also, multiplexer address information is supplied to the computer 44 through the control unit 70 for use by the computer in controlling operation of the multiplexer. A keyboard 72 may be included for manual supply of information to the computer, such as the name of the subject being tested, etc. Data display and recording unit 74 may be used a display and/or record information output from the computer, such as systolic slope, systolic and diastolic blood pressure, or the like.

Figure 5A:
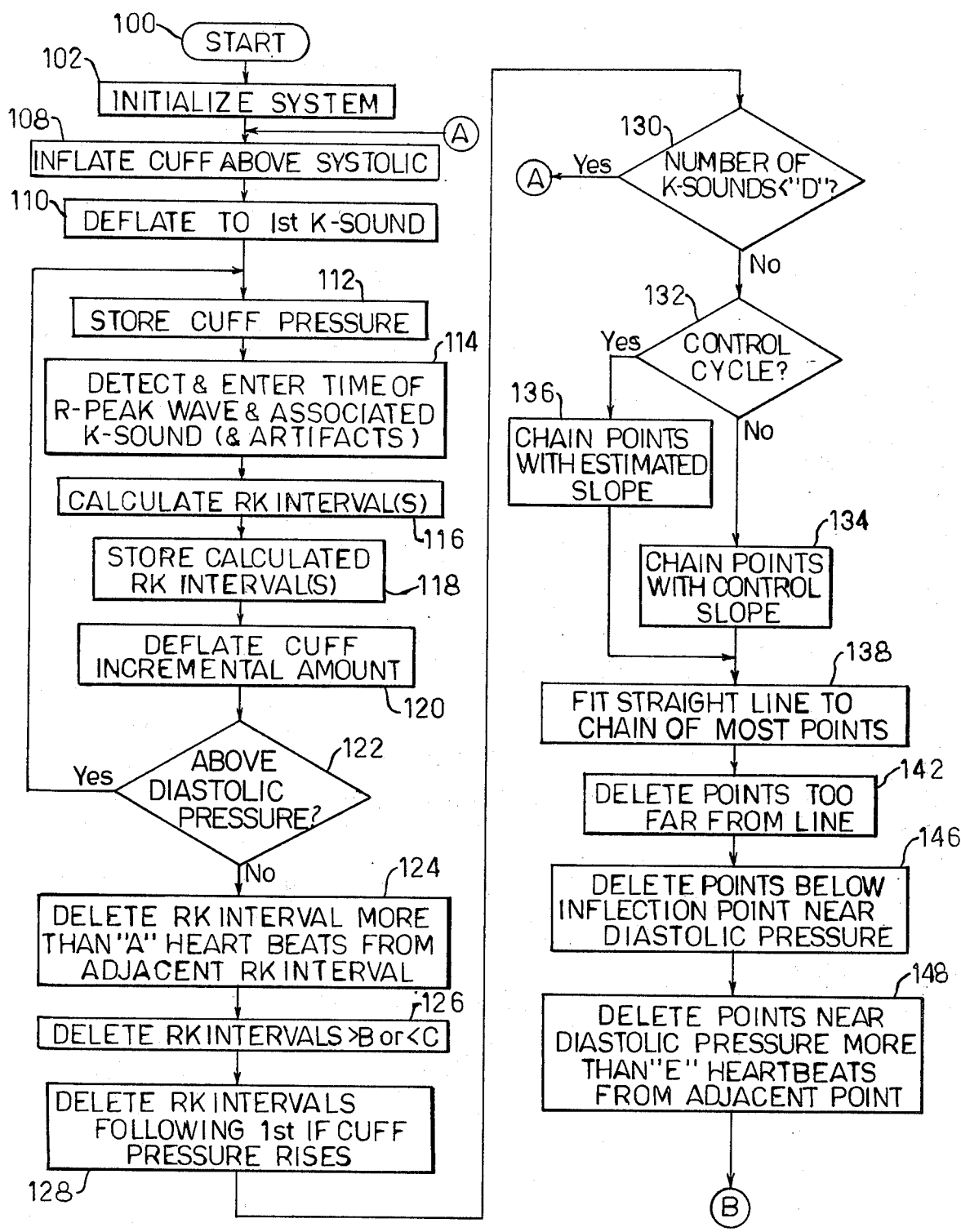
FIGS. 5A and 5B, together, show a flow chart for use in explaining operation of this invention.
Figure 5B:
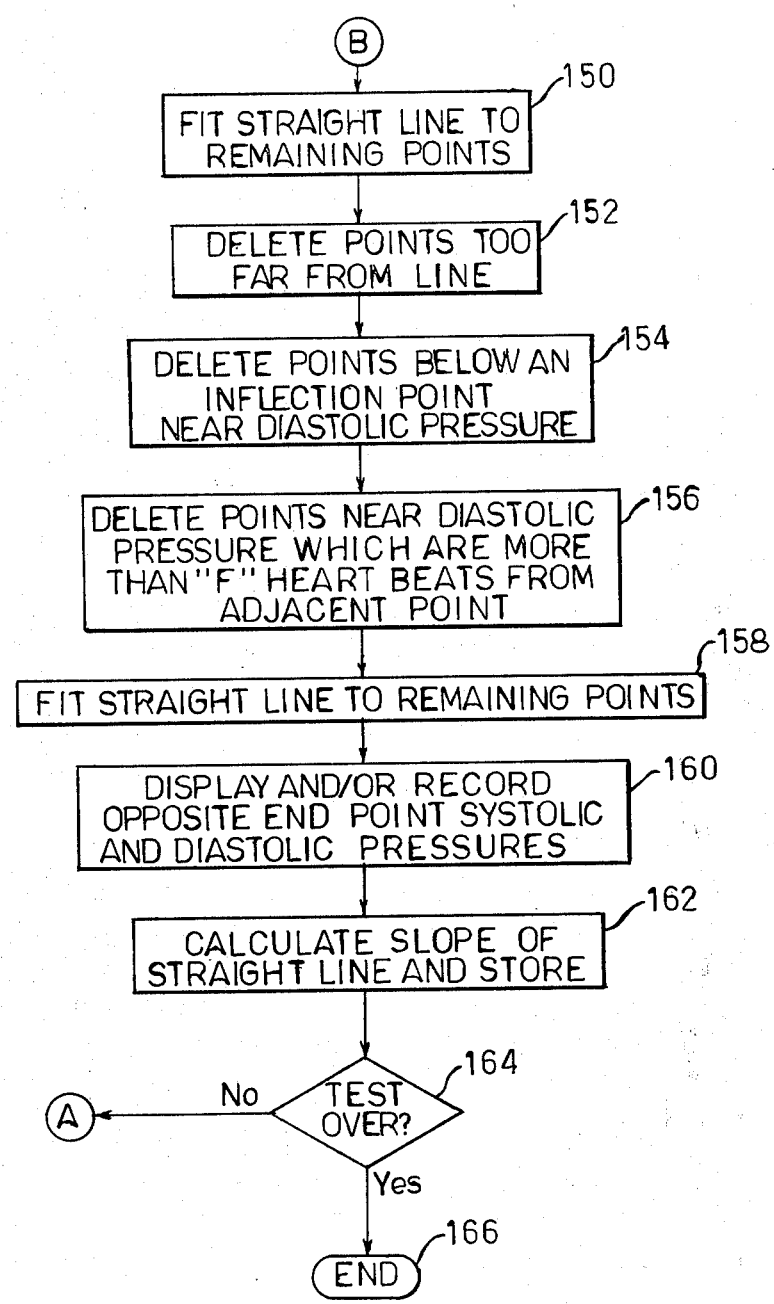

The computer 44 implements a novel process for identifying, and eliminating, artifacts included with true K-sound signals in order that accurate blood pressure and/or systolic slope measurements may be obtained using only true K-sounds. The process, in general, will be best understood with reference to the flow chart of FIGS. 5A and 5B. It will here be noted that one or more programming steps may be involved in the actual implementation of the indicated operation. Since the programming of such steps for the indicated operations is well within the skill of the average programmer, a complete program listing is not required and is not included herein.

With the cuff 30 and transducers 36 and 60 properly secured to the subject, the test is started as indicated by START step 100, at which time system power is turned on or a reset operation is performed, by means not shown. Initialization step 102 includes initial settings of counters, registers and the like, in the computer 44. A control slope $m_c$ is used by the algorithm for identifying, and discarding, artifacts. For the first activity, R-peak, K-sound and cuff pressure measurements are obtained while the subject is at rest. Measurements obtained during this resting activity are used for computing an initial control slope $m_c$. As noted above, the K-sound detector output is relatively free of artifacts while the subject is at rest, thereby ensuring that a relatively accurate value of control slope $m_c$ is computed.

With the subject at rest, before exercise, cuff inflation step 108 is entered wherein the cuff 30 is inflated under control of the computer to a pressure above systolic blood pressure through operation of the cuff pressure controller 34 to occlude blood flow in the brachial artery. Next, at step 110, the cuff pressure is reduced to a pressure at which true Korotkov, or artifact, sounds are first detected which, for true Korotkov sounds, is the systolic blood pressure. At this point, the cuff pressure is entered into the computer memory 44A through use of the transducer 36, amplifier 38, A/D converter 40 and digital multiplexer 42, as indicated by step 112.

Figure 1:
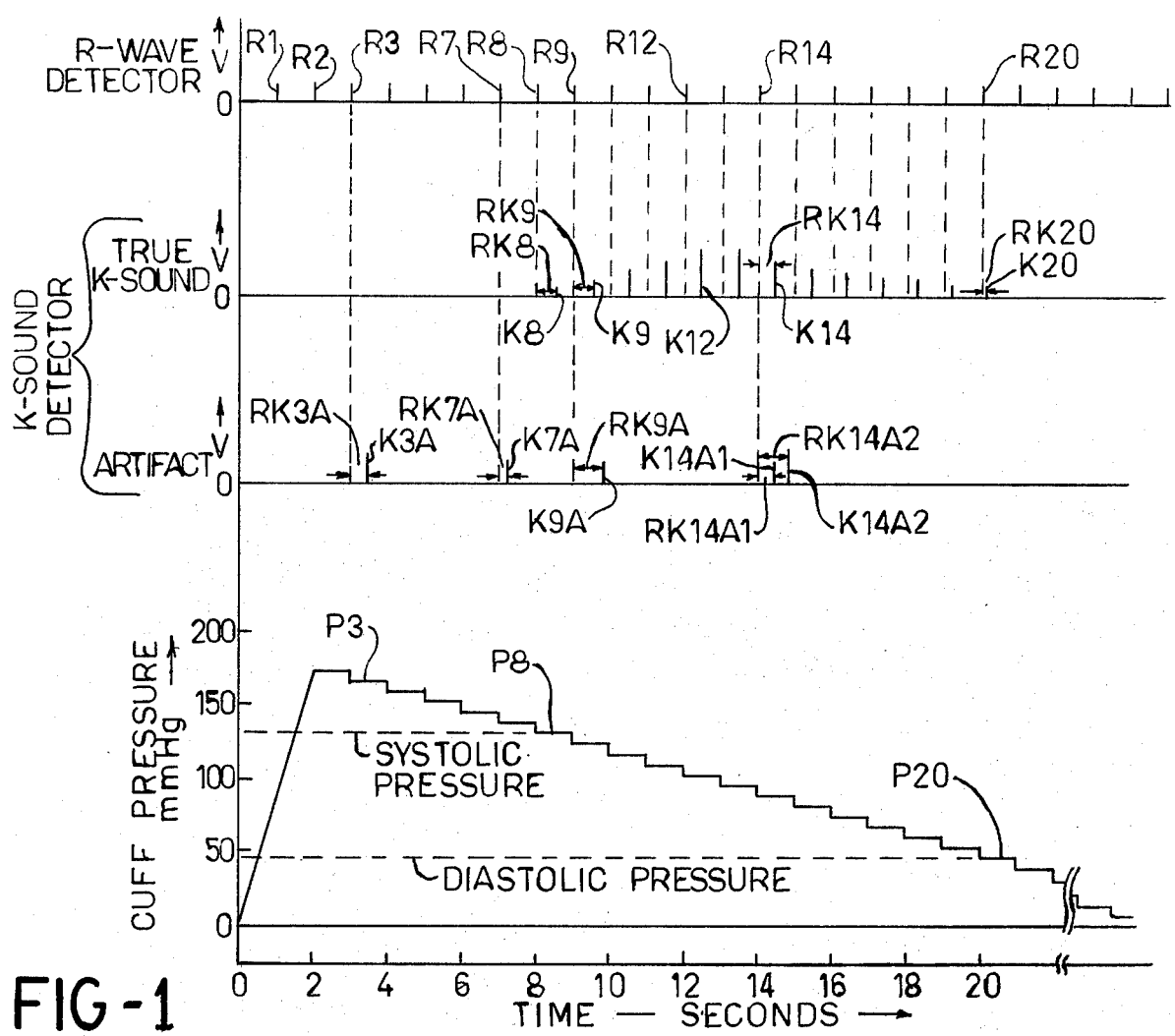
FIG. 1 shows peak R-wave detector, K-sound detector, and cuff pressure transducer output measurements obtained from a subject, plotted against time.
Figure 2:
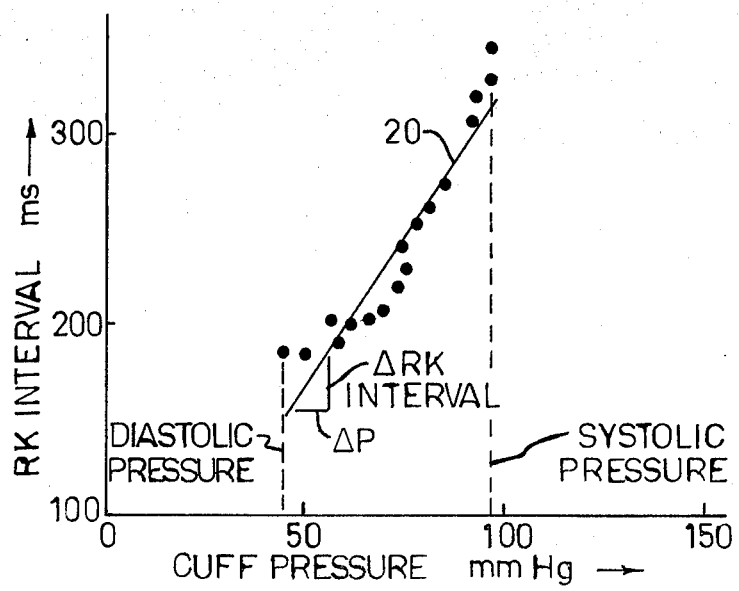
FIG. 2 is a plot of RK interval versus cuff pressure with no artifacts present.
Figure 3:
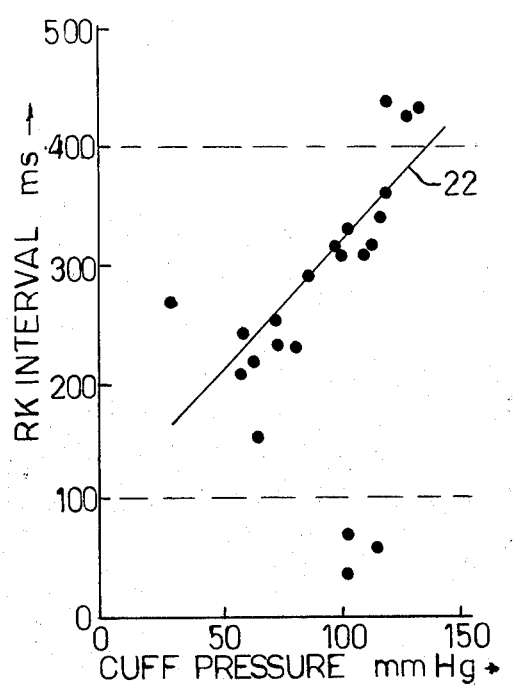
FIG. 3 is a plot of RK interval versus cuff pressure which is similar to that of FIG. 2 but which results when artifacts are included in the output from the K-sound detector used in making the measurements.

Next, at step 114, an R-peak wave is detected and its time of arrival is entered into the computer memory. The time of arrival of an associated Korotkov sound also is entered into the computer memory, as is the time of arrival of artifacts, if any, in the K-sound detector output. As seen in FIG. 1 and described above, for any given R-peak wave, the time of arrival of the true K-sound and that of one or more artifacts may be stored.

At step 116 the RK interval is calculated, and the RK interval value, or values, are stored (step 118) with the associated cuff pressure. The cuff pressure, at step 120, is then reduced an incremental amount of, say, 4 mmHg. The decision step 122 next is performed to determine whether or not cuff pressure remains above diastolic pressure. If the decision is affirmative, step 112 is again entered, whereupon the new reduced cuff pressure value is stored, together with new associated RK interval values.

When the cuff pressure is reduced below diastolic pressure, decision step 122 is negative, and step 124 is entered and the process of eliminating artifacts from the K-sound detector output begins. At step 124, RK intervals calculated at step 116 are checked for the presence of an interval which is more than a predetermined number, A, of heartbeats from an adjacent RK interval. Any RK interval which is more than, say, 3 heartbeats from an adjacent interval is deleted from the list of RK intervals stored at step 118. In FIG. 1, RK interval RK3A (occurring at heartbeat period 3) is more than three heartbeats from the nearest RK interval (here, RK7A at heartbeat period R7) and, in accordance with step 124 is deleted from the store of RK intervals obtained during the illustrated cuff deflation. Generally, such isolated RK intervals result from artifacts and should not be included in subsequent computations.

For any subject under any exercise condition, RK intervals are practically never less than 100 ms and rarely are greater than 400 ms. At step 126, the store of RK intervals is checked and those intervals equal to or less than B, say, 100 ms or equal to or greater than C, say, 400 ms, are deleted from the list. Minimum values employed in this test may range, for example, from 25 to 150 ms, and maximum values from 350 to 600 ms.

Under certain conditions during a cuff deflation, the cuff pressure may rise, due, for example, to physical pressure exerted thereon during exercise. At step 128, the cuff pressure is checked for any rise therein which may have occured during a cuff deflation. If there has been a pressure rise during a heartbeat period, only the first-occuring RK interval is accepted, and any subsequent RK intervals which may occur during the period are deleted. K-sound detector outputs which occur during the pressure increase often are produced by sounds generated by such increase and are assumed to be artifacts.

At decision step 130, the total number of RK intervals remaining following steps 124 through 128 is checked. If the number is less than, D, the RK intervals for the deflation are not processed, and operation returns to step 108 for the start of another cycle of operation. With 4 mmHg steps during cuff deflation, a plurality of true K-sounds normally are produced. For this test, a value of D in the range of between 4 and 10 typically is employed. It will be apparent that steps 124 through 128 may be performed in any desired order.

Figure 6:
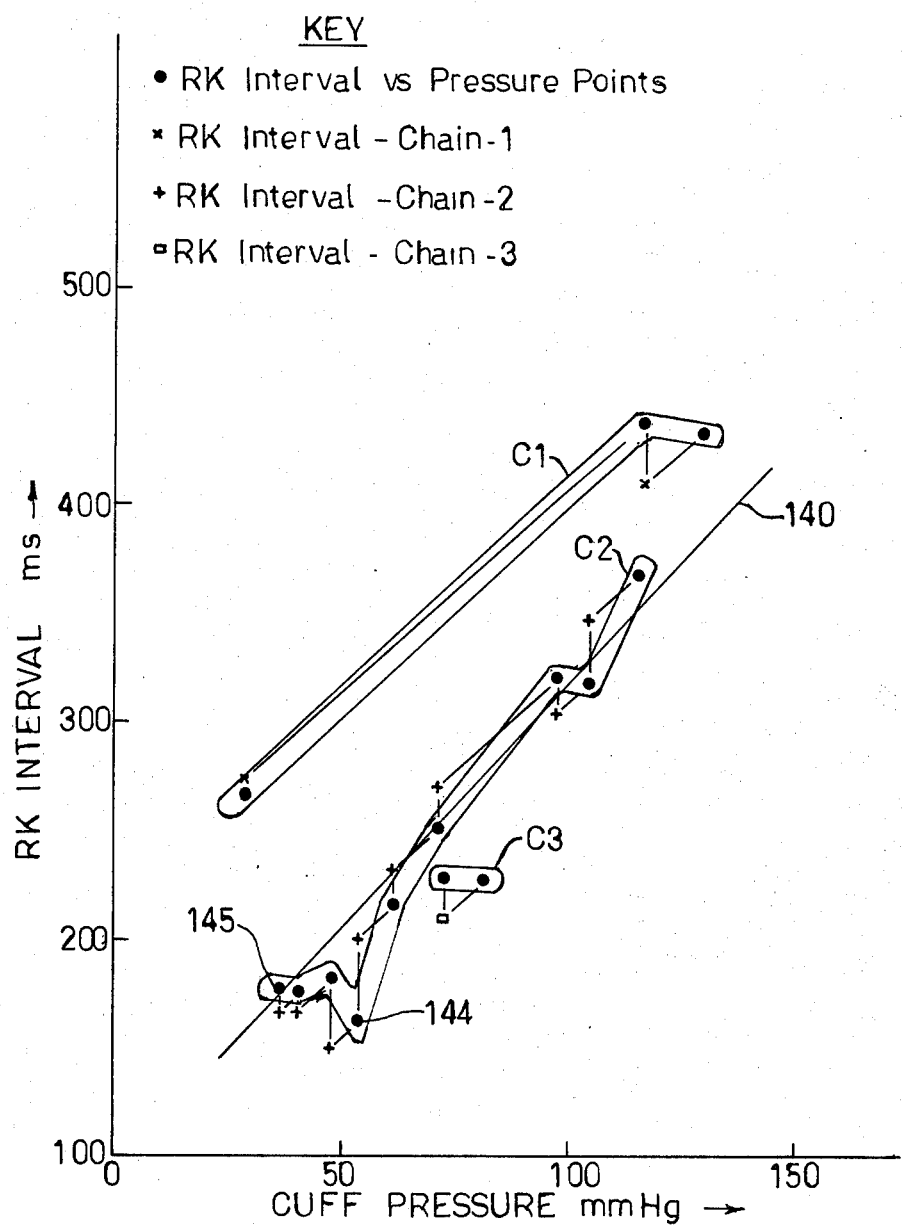
FIG. 6 is a plot of RK interval versus cuff pressure showing points thereof joined in separate groups.

If a sufficient number of RK interval points remain after step 130, another decision step 132 is entered at which a determination is made whether or not a control cycle is being processed. As noted above, once a control slope $m_c$ has been determined, such a control slope, or some function thereof, may be used in subsequent chaining operations. Chaining involves grouping together RK interval points, in a manner described below, to eliminate those points which fail to fit the group which includes the most points. If a control slope has been determined during a prior cycle, or cycles, operation, such control slope is used in the chaining operation which follows, as indicated at step 134. If no such control slope has been established, an estimated slope is used for the chaining operation, as indicated at step 136. In FIG. 6, a plot of RK interval versus cuff pressure is shown wherein three groups, or chains, of RK interval points have been established using the chaining process of this invention, the groups being identified by reference characters C1 through C3. Details involved in the chaining steps 134 and 136 are included in the flow chart of FIG. 7, described below following completion of the description of the flow chart of FIGS. 5A and 5B.

The chain which includes the greatest number of RK interval points established at step 134, or at step 136, is selected for the next step 138 where a straight line is fitted to the chain using a minimum mean-squared algorithm. In FIG. 6, straight line 140 is shown fitted to chain C2 in accordance with step 138 of the flow chart. At step 142, the distance of the RK interval points in the chain from the straight line 140 is determined, and all points more than a specified distance therefrom are deleted from the chain. For example, RK interval points more than, say, 20 ms from the line 140 may be deleted. In FIG. 6, RK interval point identified by reference character 144 is eliminated by operation of step 142.

At step 146, a check of RK interval points adjacent the diastolic end of the chain is made to determine whether or not the RK interval of the end point is less than that of its neighboring point. An end point (such as point 145 shown in FIG. 6) having an RK interval greater than the neighboring point is deleted from the chain. When an end point is deleted, the above test is repeated until an end point having an RK interval which is less than the neighboring point is located. In this manner, a point in the chain adjacent diastolic pressure at which there is an upward deflection of the chain is selected as an end point.

Next, at step 148, another check of points adjacent the diastolic end of the chain is made for any point, or group of, say, two points which is more than E heartbeats from an adjacent point, where E is, say, 3. Such point, or group of points, is deleted from the chain as likely being artifacts.

At the following step 150, a straight line is fitted to the remaining points of the selected chain using the minimum mean-squared algorithm in the manner of step 138. Steps 152, 154 and 156 which follow are similar to the above-described steps 142, 146 and 148 respectively, except the operations now are performed on the chain of RK interval points and straight line fitted thereto at step 150. At step 158, another straight line is fitted to the points which remain. The cuff pressures at the shortest and longest RK intervals included in the chain are a measure of the respective diastolic and systolic blood pressure of the subject, which pressure measurements may be displayed, stored, recorded or the like, as indicated at step 160. The slope of the straight line fitted at step 158 is determined at step 162, which slope provides a measure of the systolic slope of the blood pressure waves during the cuff deflation. This value may be stored, recorded, displayed, or the like, as desired. At decision step 164, step 108 is reentered if the test is to be continued. If not, the test is ended at step 166.

Figure 7:
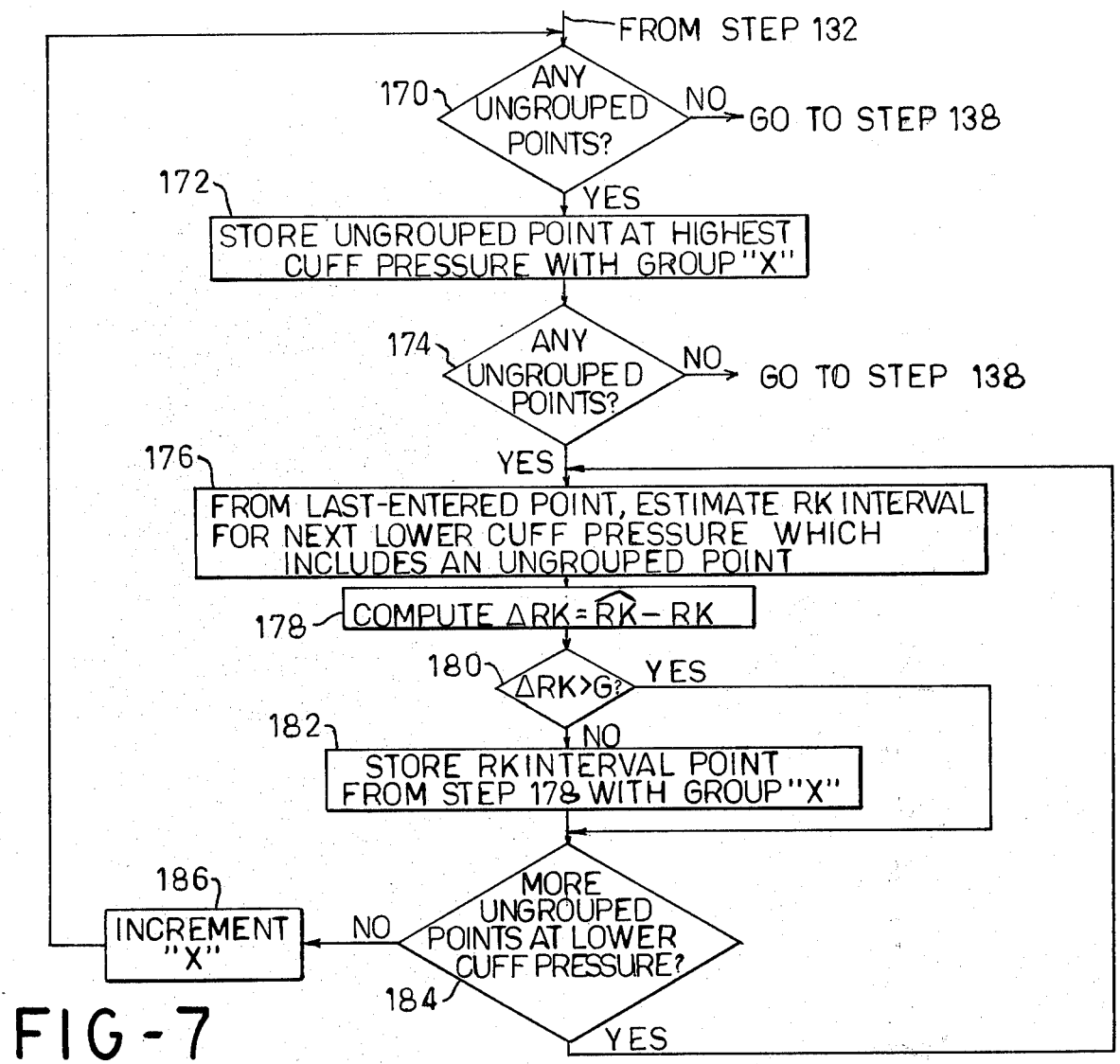
FIG. 7 is a flow chart showing details of a chaining operation included in steps of the flow chart of FIGS. 5A and 5B.
Figure 8:
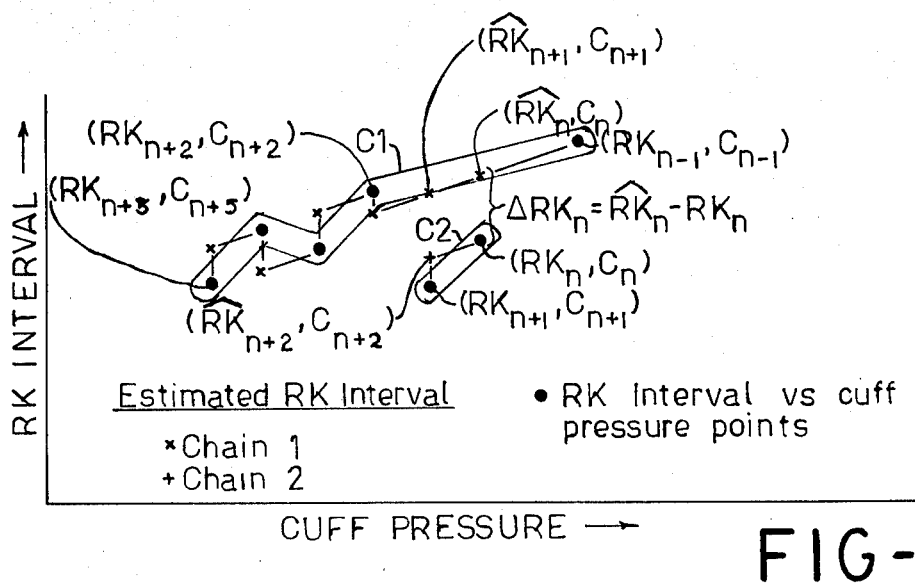
FIG. 8 is a plot of RK interval versus cuff pressure for use in explaining the chaining operation depicted in FIG. 7.

Reference now is made to the flow chart of FIG. 7 which includes details of the chaining operation shown at step 134 of FIG. 6A. As noted above, chaining involves the dividing of RK interval versus cuff pressure points obtained during a cuff deflation into groups. At step 170, a check is made for any ungrouped points. Of any remaining points, that point at the highest cuff pressure is stored in a first group of points at step 172. Referring to the RK interval versus cuff pressure plot of FIG. 8, at the beginning of the chaining operation, point $(RK_{n-1}, C_{n-1})$, which is the highest upgrouped cuff pressure point, is stored in group, or chain, 1 (one) of points at this step. Next, at step 174, another check is made for any ungrouped points and, if any points remain, an estimate of the RK interval for the next lower cuff pressure point is made at step 176. In FIG. 8, the point at the next lower cuff pressure is point $(RK_n, C_n)$. An estimated RK interval $\hat{RK}_n$ for cuff pressure $C_n$ is computed by projecting a line with a control slope $m_c$ from point $(RK_{n-1}, C_{n-1})$ to $C_n$. The difference between the estimated and actual RK values is determined at step 178. In FIG. 8, this difference is identified as $\Delta RK_n = \hat{RK}_n - RK_n$. If an artifact is present, the absolute difference $\Delta RK_n$ almost always falls outside the 40 ms, range, and at step 180 $\Delta RK_n$ is compared to, say, 40 ms to determine whether or not it is within the 40 ms range. If it is within this range, the point $(RK_n, C_n)$ is stored in a group with point $(RK_{n-1}, C_{n-1})$ at step 182, and decision step 184 is entered. If not within range, decision step 184 is entered without storing, or grouping the point. For the plot of FIG. 8, point $(RK_n, C_n)$ is outside the range whereby point $(RK_n, C_n)$ is not stored with the group 1 points.

At step 184, a check for additional points at lower cuff pressures is made. If it is determined that one or more such points remain, step 176 is reentered, wherein an estimated RK interval for the next lower cuff pressure point is made. In FIG. 8, the next lower cuff pressure point is $(RK_{n+1}, C_{n+1})$, and the estimated point is $(\hat{RK}_{n+1}, C_{n+1})$. Again, the difference in RK interval between the actual and estimated points exceeds 40 ms, whereby this point also is not included with the group 1 points.

The next lower cuff pressure point ($RK_{n+2}$, $C_{n+2}$) is checked and the $\Delta RK_n$ is determined to be within the 40 ms range. Now, the result of decision step 180 is negative, whereupon step 182 is entered for storage of point ($RK_{n+2}$, $C_{n+2}$) with the group 1 points.

In accordance with the present invention, when a new RK interval vs cuff pressure point is added to the group, a line with the control slope $m_c$ is projected from the newly added point to the next lower cuff pressure which includes an ungrouped point. As seen in FIG. 8, a new line with slope $m_c$ is shown projected from point ($RK_{n+2}$, $C_{n+2}$) newly added to the list. This method of chaining provides for much more accurate grouping of points than is provided in the arrangement disclosed in the above mentioned article, "A Study of Noninvasive Blood Pressure Measurement Techniques" wherein the line is projected from the highest cuff pressure points to the lowest, and not from newly added points.

In FIG. 8, it will be seen that ($RK_{n+5}$, $C_{n-5}$) is the last point to be added to chain 1. At this point in the operation, decision step 184 is negative, whereupon the group number is incremented at step 186, and decision step 170 is reentered. If more ungrouped points exist, the chaining operation is repeated starting with the point at the highest cuff pressure not yet included in a chain, or group. In FIG. 8, point ($RK_n$, $C_n$) is selected at step 172 for storage with points of a second group. After point ($RK_{n+1}$, $C_{n+1}$) has been identified as a group 2 point, at step 180, and stored at step 182, no more ungrouped points at a lower cuff pressure remain, and the operation loops back through step 186 to step 170. Now, since there are no remaining ungrouped points, decision step 170 is negative, and step 138 (FIG. 5A) is entered for fitting of a straight line to the group which includes the greatest number of points in the manner described above.

Step 136 involves essentially the same operations as above-described step 134 except that an estimated slope rather than a control slope is used in projecting a line from one point to a next lower cuff pressure which includes a point. As noted above, the estimated slope is used during a control cycle during which the subject is stationary, and artifacts are at a minimum. The slope of the straight line fitted to points at step 158 and calculated at step 162 during a control cycle is employed in step 134 on subsequent cuff deflations during which the subject is active. If desired, a plurality of control cycles may be performed, and the average slope obtained therefrom may be used as the control slope.

The slope of the line fitted at step 158 normally changes during exercise. For any given cuff deflation, the slope obtained during one or more preceeding cuff deflations, or some function thereof, may be used in step 134 as the control slope. The cuff deflation cycles may be repeated often enough such that the change in slope between cycles is minimal. Thus, the slope obtained during one cuff deflation may provide an accurate control slope for use in a next cycle. In an alternative arrangement, an estimated stope of, say, 1 may be employed in all chaining operations, without establishment of a control slope.

The invention having been described in detail in accordance with requirements of the Patent Statutes various other changes and modifications will suggest themselves to those skilled in this art. For example, the novel method is not limited to use with apparatus illustrated in FIG. 4. Instead of using R-wave and K-sound detectors, the ECG signal and/or Korotkov sound waveforms may be digitized, and the digital signals supplied to the computer for software R-wave and/or K-sound detection, with the time of arrival of the software R-wave and/or K-sounds being stored in the computer memory. Also, a recording of the necessary inputs may be made, and the recorded signals/played back to provide the computer inputs. Such recording of signals for processing is particularly useful for long term monitoring of blood pressure of ambulatory subjects. Portable equipment for automatic cuff inflation and deflation, and K-sound, ECG and cuff pressure recording is well known. Obviously, high speed playback of the recorded signals is possible, so long as compensation is made for any time differences, if any, which may result therefrom. It is intended that the above and other such changes and modifications shall fall within the spirit and scope of the invention defined in the appended claims.

We claim:

1. A machine implemented method for identifying and removing artifacts in Korotkov sound signals for use in a system for measuring systolic and diastolic blood pressure, obtaining a measure of the systolic slope of blood pressure waves, or the like, comprising the steps of:
   (1) recurrently obtaining cuff pressure measurements and arrival times of peak R-wave signals and Korotkov sound signals including artifacts through the active K-sound range of a cuff pressure deflation,
   (2) using arrival times of associated R-wave signals and Korotkov sound signals and artifacts, determining RK intervals from which a plurality of RK interval versus cuff pressure points are obtained, some of which are true points and others of which are artifact points,
   (3) processing said points to group the same such that one group includes substantially only true points, said processing comprising;
      (a) from an existing point at high cuff pressure, estimating an RK interval value $\hat{RK}$ for a next lower cuff pressure which includes a point,
      (b) including the point at said lower cuff pressure in a group which includes also said existing point when the difference $\Delta RK = \hat{RK} - RK$ at a lower cuff pressure is within a predetermined range, and not including the point at said lower cuff pressure in the group when the difference $\Delta RK$ is outside said predetermined range,
      (c) repeating steps 3a and 3b but using the last included point in the group for estimating an RK interval value for a next lower cuff pressure which includes a point,
      (d) repeating steps 3a, 3b and 3c using ungrouped points until all points are included in a group, and
   (4) selecting as the one group which includes substantially only true points that group which includes the greatest number of points.

2. In a method as defined in claim 1 wherein estimating an RK interval value $\hat{RK}$ includes projecting a line with slope m from an RK interval versus cuff pressure point.

3. In a method as defined in claim 2 wherein the slope m is an estimated slope.

4. In a method as defined in claim 3 wherein an estimated slope of substantially 1 is employed wherein the RK interval value is in units of ms and cuff pressure is in units of mmHg.

5. In a method as defined in claim 2 wherein a slope m, used in estimating an RK, interval value $\hat{RK}$ is a function of slope m established during a preceeding cuff deflation cycle.

6. In a method as defined in claim 1 which includes deleting from said one group any points adjacent diastolic pressure having RK intervals larger than the smallest RK interval at cuff pressures less than said cuff pressure at said smallest interval.

7. In a method as defined in claim 1 which includes, using minimum mean-squared fitting techniques, fitting a straight line to said one group of points, and repeating steps 3(a) through 3(c) using the slope of the straight line to obtain the estimated value $\hat{RK}$.

8. A machine implemented method as defined in claim 1 including the step of
   (5) from the selected one group of substantially only true points from step (4), obtaining a measure of systolic and diastolic blood pressures from points adjacent the respective upper and lower ends of cuff pressures.

9. A machine implemented method as defined in claim 1 including the step of
   (5) fitting a straight line to at least some points of the selected one group of substantially only true points from step (4), the slope of said straight line providing a measure of the systolic slope of the blood pressure waves during cuff deflation.

10. In a blood pressure monitoring system for measuring blood pressure, obtaining a measure of the systolic slope of blood pressure waves, or the like, the combination comprising,
    (1) an inflatable cuff adapted to encircle a subject's arm,
    (2) means for inflating and deflating said cuff within a range of pressures within which Korotkov sounds are produced,
    (3) pressure transducer means responsive to cuff pressure and having an output signal related thereto,
    (4) electrode means for sensing electrocardiographic signals from the subject,
    (5) means for detecting the R-wave in the electrocardiographic signals,
    (6) transducer means for sensing Korotkov and artifact sounds during a cuff deflation,
    (7) means for detecting Korotkov and artifact sounds in the output from said sound transducer means,
    (8) means for accumulating a plurality of cuff pressure measurements and associated RK intervals comprising the time between the occurrence of an output from the R-wave detecting means and the associated signals from the Korotkov and artifact sound detecting means during a cuff deflation to establish a plurality of RK interval versus cuff pressure points, some of which are true points and others of which are artifact points,
    (9) machine implemented means for grouping true points to identify and distinguish the same from artifact points comprising
      (a) means responsive to one point at a high cuff pressure for estimating an RK interval, $\hat{RK}$, for a true point at a next lower cuff pressure which includes a point,
      (b) means for including said point at said next lower cuff pressure in a group which includes said one point if the difference, $\Delta RK$, between the estimated RK interval value, RK, and the RK interval value at said next lower cuff pressure is within a predetermined range, and not including said point if the difference, $\Delta RK$, is outside said range,
      (c) means for repeating operations performed by elements 9a and 9b using the last-added point to the group for estimating RK until no ungrouped point at a lower cuff pressure remains,
      (d) means for repeating operations performed by elements 9a, 9b and 9c until all points are included in a group, points identified by element 9d being included in another group of points each repetition of element 9d operations,
    (10) means for identifying the group with the largest number of points as a group of substantially all true points.

11. In a blood pressure monitoring system, or the like, as defined in claim 10 wherein said means for estimating RK also is responsive to a line of slope m projected from said one point.

12. In a blood pressure monitoring system, or the like, as defined in claim 11 wherein the slope m comprises an estimated slope value stored in the computer.

13. In a blood pressure monitoring system as defined in claim 10 including,
    means for obtaining a measure of systolic and diastolic blood pressures from points adjacent the upper and lower ends, respectively, of cuff pressures of the group of substantially all true points.

14. In a blood pressuring monitoring system as defined in claim 10 including,
    means for fitting a straight line to at least some of the points of the group of substantially all true points, the slope of said straight line comprising a measure of the systolic slope of blood pressure waves during cuff deflation.

* * * * *